United States Patent [19]

Sutton

[11] Patent Number: 4,850,054

[45] Date of Patent: Jul. 25, 1989

[54] MULTIPURPOSE SUN VISOR

[75] Inventor: Kim C. Sutton, St. Charles County, Mo.

[73] Assignee: Sutton Industries, Inc., St. Peters, Mo.

[21] Appl. No.: 173,142

[22] Filed: Mar. 25, 1988

[51] Int. Cl.$^4$ ............................ A42B 1/00; A61F 9/00
[52] U.S. Cl. ........................................ 2/191; 446/27; 2/DIG. 11
[58] Field of Search ................... 2/9, 13, 175.1, 181, 2/182.6, 191, 192, 195, 197, 427, 428, 209.3; 446/27, 404

[56] References Cited

U.S. PATENT DOCUMENTS

| | | | |
|---|---|---|---|
| 1,598,313 | 8/1926 | Rosenberg | 2/182.6 |
| 2,116,736 | 5/1938 | Subira | 2/191 |
| 2,333,336 | 11/1943 | Powell | 2/428 |
| 2,541,242 | 2/1951 | Grove | 2/13 |
| 2,598,265 | 5/1952 | Jones | 2/427 |
| 2,629,874 | 3/1953 | LaMaida | 2/192 X |
| 2,682,666 | 7/1954 | Mayer | 2/192 X |
| 2,765,472 | 10/1956 | Schoen-Wolski | 2/195 |
| 2,827,636 | 3/1958 | Hoeflich | 2/195 |
| 2,988,743 | 6/1961 | Wagenfeld | 2/197 X |
| 3,131,401 | 5/1964 | Brown | 2/175 |
| 3,164,842 | 1/1965 | Weinstein | 2/195 |
| 3,557,386 | 1/1971 | Fisher | 2/191 |
| 3,908,199 | 9/1975 | Lim | 2/175 |
| 4,222,125 | 9/1980 | Sewell-Wood | 2/192 X |
| 4,258,437 | 3/1981 | Sawatsky | 2/192 X |
| 4,393,519 | 7/1983 | Nicastro | 2/DIG. 11 X |
| 4,429,420 | 2/1984 | Wolff | 2/175 X |
| 4,481,680 | 11/1984 | Mason et al. | 2/181 X |
| 4,670,910 | 6/1987 | Rosasco | 2/209.3 X |
| 4,701,965 | 10/1987 | Landis | 2/9 X |
| 4,768,231 | 9/1988 | Schrack | 2/13 X |

Primary Examiner—Werner H. Schroeder
Assistant Examiner—Jeanette E. Chapman
Attorney, Agent, or Firm—Gravely, Lieder & Woodruff

[57] ABSTRACT

A blank formed from a flexible sheet material has arcuate inner and outer margins and straight margins which diverge from the inner margin to the outer margin. In addition, the blank has inner and outer arcuate score lines which generally follow the contours of the inner and outer margins, and divide the blank into a main panel located between the score lines, an abutment panel located between the inner score line and the inner margin, and a narrow lip located between the outer score line and the arcuate outer margin. The abutment panel folds downwardly with respect to the main panel along the inner score line, while the lip folds upwardly along the outer score line. These folds impart an upward bow to the main panel, yet hold the main panel oblique to the abutment panel so that it does not drop too far downwardly when the abutment panel is held against the user's forehead with an elastic head band. This band attaches to the main panel such that the force exerted on the visor by it directs the lower margin of the abutment panel slightly away from the user's forehead so as to avoid discomfort. The main panel near one of its side margins has a slit and near the other one has a tab which with fits into and interlocks with the slit. This enables the blank to assume a conical configuration in which is functions as a megaphone. The megaphone easily becomes a party hat. Several of the blanks, when folded into visors, may be attached together end-to-end at the tabs and slits, to form a sun shade.

23 Claims, 4 Drawing Sheets

4,850,054

MULTIPURPOSE SUN VISOR

BACKGROUND OF THE INVENTION

This invention relates in general to sun visors and more particularly to a sun visor that is adaptable to other uses.

Sporting events held in open stadiums attract large numbers of spectators and as such represent a popular form of entertainment. By far the greatest number of these events occur during the summer and fall of the year, seasons when the sun is least likely to be obscured. Indeed, the sun creates considerable glare, and many spectators find it necessary to wear a visor of one type or another. Aside from that sporting events generate considerable spirit, and it is not uncommon for spectators to purchase clothing and other accessories bearing the names and symbols of teams participating in the contests.

The present invention concerns a sun visor which comfortably conforms to the user's head, and further may be easily converted to several other uses, namely a megaphone, a fan, a more expansive sunshade, or a party hat. Moreover, the visor has a large surface area to which the name or symbol of a sporting team or some other organization may be applied or on which an advertising message may be placed, and as such the visor is ideally suited for sale at sporting events.

DESCRIPTION OF THE DRAWINGS

In the accompanying drawings which form part of the specification and wherein like numerals and letters refer to like parts wherever they occur.

DETAILED DESCRIPTION

Figure 1:
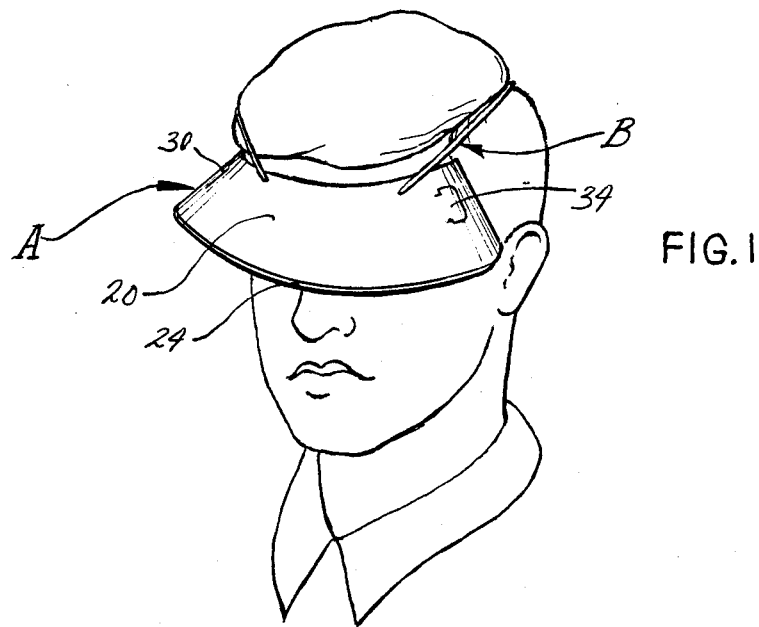
FIG. 1 is a perspective view of the sun visor of the present invention shown as it would normally be worn.
Figure 2:
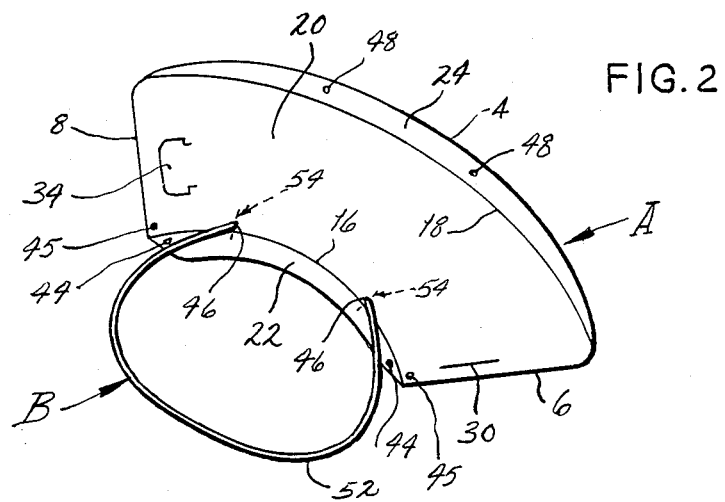
FIG. 2 is a perspective view of the sun visor in the configuration it would normally be worn, the perspective being from the rear looking over the inner portion and top of the visor.
Figure 3:
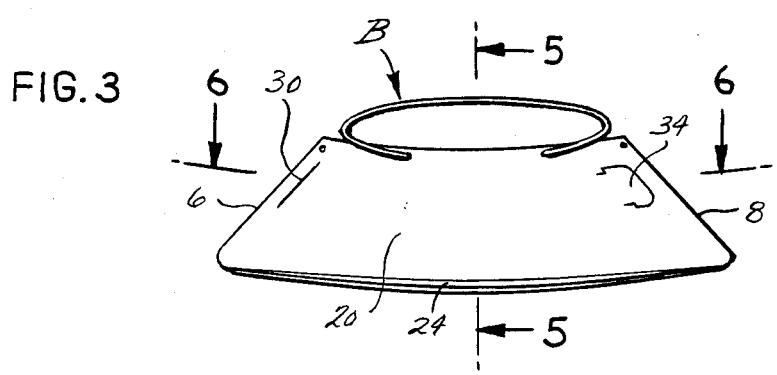
FIG. 3 is a front elevational view of the visor in the configuration in which it is normally worn.
Figure 4:
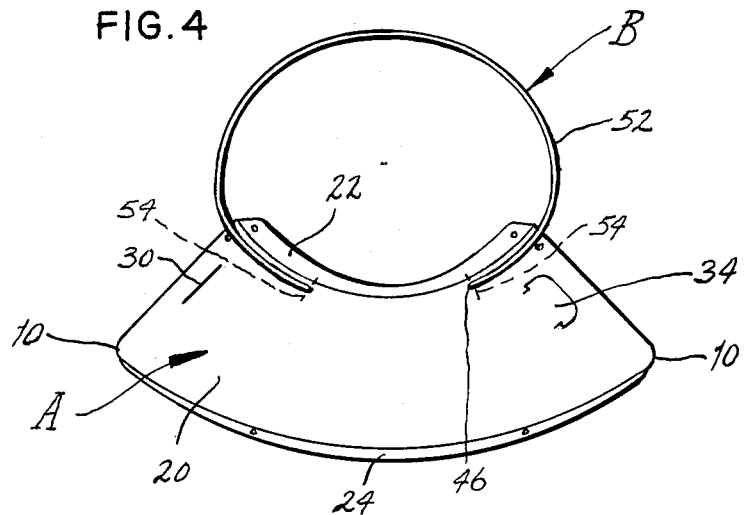
FIG. 4 is a plan view of the visor in the configuration that is normally worn.

Referring now to the drawings, a sun visor A (FIG. 1) fits comfortably against the forehead of the user where it is held in place by an elastic band B which extends from the visor along the sides of and around the back of the user's head. When in place, the visor A is inclined downwardly from the user's forehead just enough to shade the user's eyes, but does not obstruct the user's vision.

Figure 7:
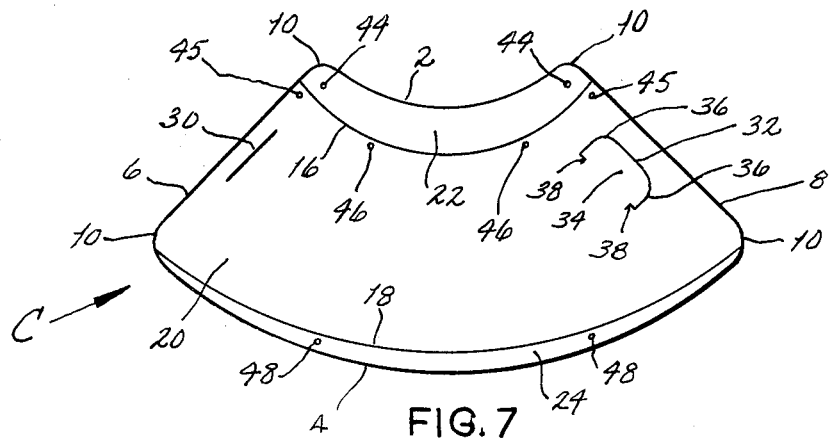
FIG. 7 is plan view of the blank from which the visor is formed.

The visor A is derived from a blank C (FIG. 7) which is cut from a flexible sheet-like material that is preferably durable and water repellant. Polyethylene is one such material, and although paperboard will also suffice, it is not nearly as durable as polymers. The thickness of the material is not too critical, although the material should be thin enough to flex relatively easily and to fold at score lines, yet thick enough to withstand forces, such as light wind loads, that might otherwise distort it. The blank C is easily converted into the visor A by making two simple folds and attaching the elastic band B.

Considering the visor A first in terms of the blank C (FIG. 7) from which it is derived, the blank C has an arcuate inner margin 2 and an arcuate outer margin 4 as well as side margins 6 and B which merge into the margins 2 and 4 at rounded corners 10. The arcuate inner and outer margins 2 and 4 lie generally concentric to each other and are thus parallel, the space between them being about 6¾ in. The side margins 6 and 8, on the other hand, are straight and diverge from the inner margin 2 to the outer margin 4, with the angle between the two being between 80° and 100° and preferably about 90°. The four margins 2, 4, 6, and 8 together with the four corners 10 constitute the border or perimeter of the blank C, but not necessarily the visor A.

The blank C contains two score lines 16 and 18, both of which generally follow the curvature of the arcuate margins 2 and 4 and extend the full width of the blank C. As such, the score lines 16 and 18 divide the blank C into three sections: namely a center or main panel 20, an abutment panel 22 and a front lip 24. The main panel 20 lies between the two score lines 16 and 18 and possesses the greatest area. The abutment panel 22 exists between the score line 16 and the inner margin 2, whereas the front lip 24 lies between the score line 18 and the outer margin 4. The former is somewhat wider than the latter, but neither occupies nearly the area of the main panel 20.

The inner score line 16 extends from the one side margin 6 to the other side margin B and intersects those margins beyond the two corners 10 at the ends of the arcuate inner margin 2. Moreover, the score line 16 lies generally concentric to the inner margin 2, but is slightly closer to the inner margin 2 at its ends than midway between its ends. Indeed, midway between their respective ends, the score line 16 and the inner margin 2 are spaced about 1 3/16 in. apart. The score line 16 permits the abutment panel 22 to be folded downwardly with respect to the main panel 20, and when the panel 22 is so folded, the main panel 20 acquires an upwardly directed bow.

The outer score line 18, in contrast to the inner line 16, does not extend out to the end margins 4 and 6, but instead terminates or runs out into the two rounded corners 10 which are located at the ends of the outer margin 4, intersecting those rounded corners 10 approximately midway between their ends. While the outer sore line 18 generally follows the curvature of the outer margin 4, it is substantially closer to that margin at its ends than midway between its ends. Indeed, the spacing between the score line 18 and the outer margin is about 7/16 in. midway between their ends, whereas at their ends it is about ⅛ in. The score line 18 enables the lip to be folded upwardly with respect to the main panel 20.

Near the side margin 6 the center panel 20 is provided with a slit 30 that lies parallel to the margin 6. Moreover, the slit 30, which is about ¾ in. long, lies somewhat closer to the score line 16 than the score line 18. The slit 30 is set about ½ in. inwardly from the margin 6.

Figure 8:
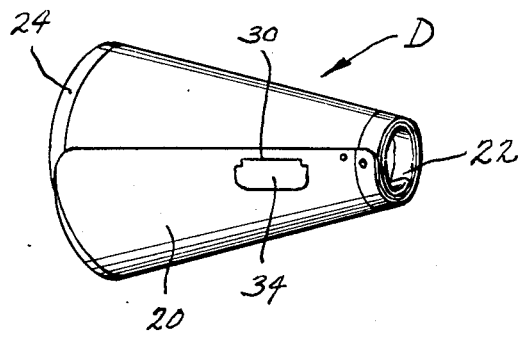
FIG. 8 is a perspective view of the visor converted into a megaphone.

On its other side adjacent to the side margin 8, the panel 20 is provided with another slit 32 which delineates a tab 34 that projects toward the margin 8. The tab 34 has rounded corners 36, and where it merges with the main body of the panel 20 it is provided with small cutouts 38. Although the tab 34 is slightly wider than the slit 30 is long, in the regions of its cutouts 38, it is slightly narrower than the slit 30 is long. When the blank C is bent into the shape of a cone, the tab 34 may be manipulated into the slit 30 and when fully inserted will engage the panel 20 at its cutouts 38, thus enabling the tab 34 to lock within the slit 30 (FIG. 8). As such the tab 34 is presented outwardly where it may be bent away from the main panel 20 to serve as a handle.

Near the rounded corners 10 at the ends of the inner margin 2, the abutment panel 22 for the blank C has small holes 44, there being one generally at the center of curvature for each of the two corners 10. The holes 46 are large enough to loosely receive the elastic band B. The main panel 20 has similar holes 45 near the ends of the score line 16, these holes being set inwardly slightly from both the score line 16 and their respective side margins 6 and 8, and still more holes 46 which are likewise located along the score line 16 but are set further inwardly, perhaps as much as 2 in. from the holes 45. As such, the spacing between the two holes 46 is slightly greater than the spacing between the holes 46 and their respective side margins 6 and 8. The holes 45 and 46 are likewise large enough to loosely receive the elastic band B. Finally, the lip 24 contains two more holes 48 which are spread such that they will be located 180° from each other when the blank C is bent into a cone and held in that configuration with the tab 34 locked into the slit 30. The holes 4B are also large enough to loosely receive the band B.

The band B includes a string 52 which is elastic and therefore can be stretched, but when released will of course return to its original length. At each of its ends, the string 52 has a metal clip 54 which is straight and connects with the string 52 generally midway between the ends of the clip 54. This enables the clip 54 to be moved into a position in which it is generally parallel to the string 52, and when so disposed, it will pass through any one of the holes 44, 45, 46 and 48 along with the string 52 to which it is connected. Once through the hole, the clip 54 turns perpendicular to that portion of the string 52 which extends from it and thus prevents the string 52 from being withdrawn through the particular hole 44, 45, 46 or 48 through which it was threaded.

Figure 5:
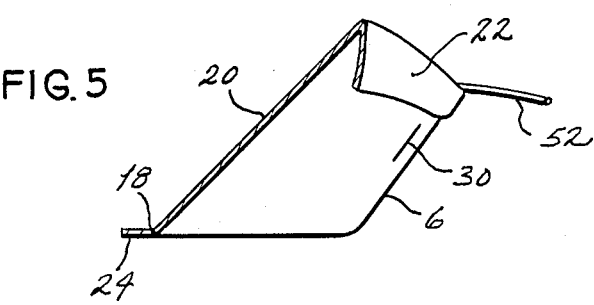
FIG. 5 is a sectional view of the visor taken along line 5—5 of FIG. 3.

The blank C is easily transformed into the visor A, and to effect the conversion the lip 24 is folded upwardly with respect to the main panel 20 along the curved score line 18 (FIG. 5). On the other hand, the abutment panel 22 is folded downwardly with respect to the main panel 20 along the score line 16, indeed at a substantially greater angle than the lip 24. These folds impart a somewhat convex configuration or bow to the main panel 20, at least transversely between its side margins 6 and 8, with the bow being greatest along the shorter score line 16. Moreover, the folds at the score lines 16 and 18 become the inner and outer margins of the main panel 20. Furthermore, the clips 54 at the ends of the string 52 of the band B are inserted through holes 46 in main panel 20 and then turned parallel to the panel 20 so that the band B cannot be withdrawn from the holes 46.

Figure 6:
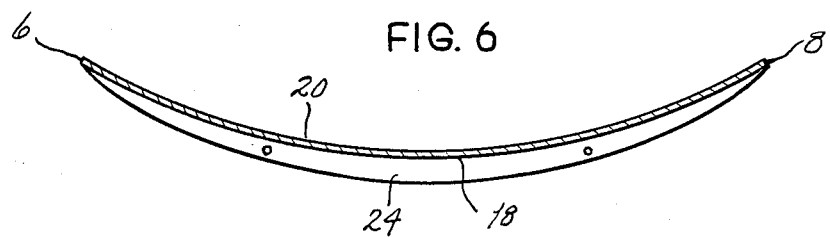
FIG. 6 is a sectional view of the visor taken along line 6—6 of FIG. 3.

With the blank C so configured, that is to provide the sun visor A, the elastic band B is stretched and fitted around the back of the user's head while the abutment panel 22 is brought against the user's forehead (FIG. 1). Once the band B is released, it contracts and holds the abutment panel 22 snugly against the forehead, the force being transmitted from the clips 54 through those small portions of the main panel 20 that lie between the holes 46 and the score line 16. Actually, the inner margin 2 is directed slightly away from the user's forehead, this being by reason of the application of the retaining force at the holes 46, so the margin 2, which is an edge, does not press into the forehead and create discomfort. In other words, the elastic band B pulls the upper portion of the panel 22 snugly against the user's forehead and causes the lower portion including the margin 2 to remain somewhat away from the forehead. The upper portion of the main panel 20 assumes the curvature of the score line 16, which is in essence against the user's forehead, but the curvature is less pronounced along the lower score line 18. In any event, the upper surface of the panel 20 acquires a convex shape from one side margin 6 to the other margin 8 (FIG. 6), curving generally over the user's eyes where it shades them from the glare of the sun. As such, the main panel 20 lies obliquely with respect to the abutment panel 22 and the user's forehead, indeed so much so that an acute angle exists between the two. Actually, the natural tendency of the panel 20 is to fold flat against the abutment panel 22, and if this occurred, the main panel 20 would completely block the user's eyes. The lip 24, when turned upwardly from the main panel 20 at an obtuse angle prevents this, for it stiffens the main panel 20 along its lower edge so that the lower region of the main panel 20 cannot assume a curvature as pronounced as the upper region. Consequently, the main panel 20 projects obliquely outwardly from the abutment pane 22, has a transverse curvature which becomes progressively less beyond the score line 16, and otherwise assumes an inclination and curvature most suitable for protecting the user's eyes from the glare of the sun.

The blank C may also be converted into a megaphone D (FIG. 8). For this transformation, the blank C, while the abutment panel 22 and lip 24 are extended from it with no break at either of the score lines 16 or 18, is bent into a conical configuration. Indeed the side margin 8 is brought over the side margin 6 and likewise over the end of the tab 34, whereupon the tab 34 is inserted through the slit 30, it being bowed slightly to reduce its width to the length of the slit 30. The tab 34 moves through the slit 30 until its cutouts 38 align with the ends of the slit 30, whereupon the sides of the tab 34 spread outwardly so that the two sides of the blank C lock together at the slit 30 and tab 34. The inner and outer margins 2 and 4 of the blank C likewise become curved, the former forming the small end of the megaphone D and the latter the large end. The tab 34 forms a handle for holding the megaphone D.

Figure 9:
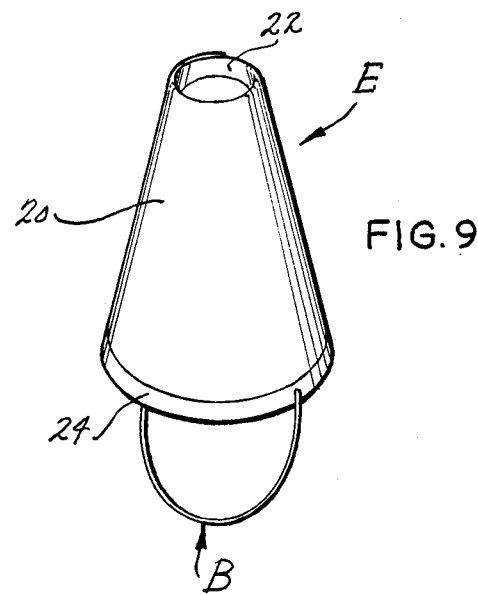
FIG. 9 is a perspective view of the visor converted into a party hat.

The megaphone D in turn may be converted into a party hat E (FIG. 9) simply by inserting the clips 54 at the ends of the elastic band B through the holes 48 in the lip 24 and then turning those clips parallel to the surface which surrounds their respective holes 48. In this regard, the holes 48 are spaced 180° apart when the tab 34 interlocks with the slit 30. The string 52 of band B loops downwardly to provide a thin strap for holding the hat E on the user's head.

Thus, the hat E is placed on the user's head with the outer margin 4, now curved into a circle, against the top of the head, and the inner margin presented upwardly. The string 52 extends downwardly along the sides of the user's head and loops under the user's chin to hold the hat E in place.

Figure 10:
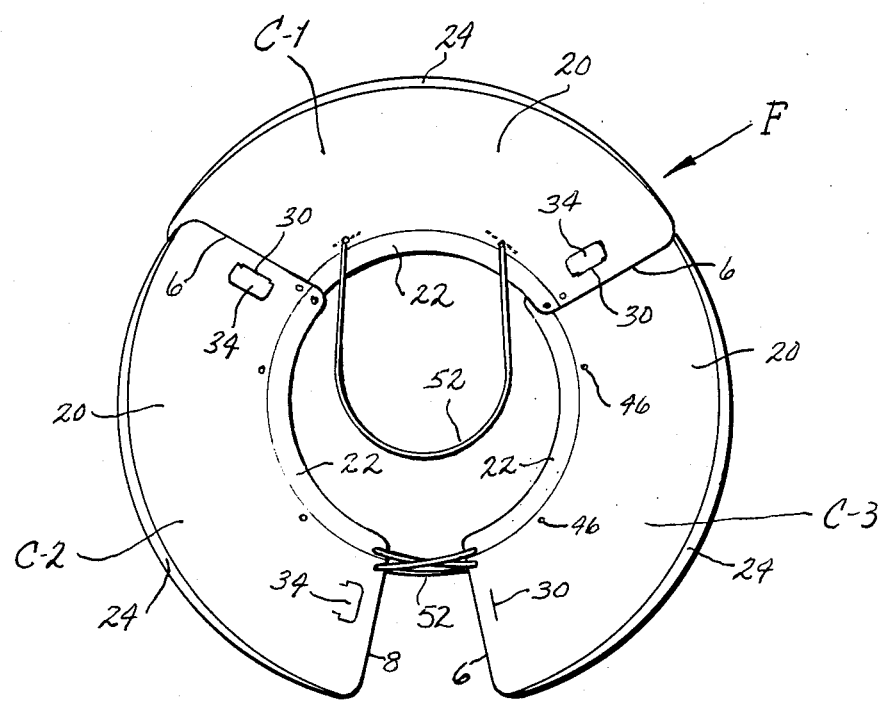
FIG. 10 is a top plan view of the sun shade formed from three visor blanks connected together end-to-end.

Several of the blanks C, preferably three of them C-1, C-2 and C-3, may be connected together end to end to provide a shade F (FIG. 10) for protecting the front and sides of the user's head from the sun. To this end, each of the three blanks C is folded along its score line lB such that the lip 24 is turned upwardly, all as with the sun visor A. Then the three blanks C-1, C-2 and C-3 are connected together end to end. In this regard, the side margin 8 on the first blank C-1 is passed under the side margin 6 of the second blank C-2, and the tab 34 of the first blank C-1 is inserted through the slit 30 of the second blank C. Indeed, the tab 34 is forced to its fullest extent into the slit 30, and accordingly interlocks with the ends of the slit 30, thus securing the two blanks C-1 and C-2 together. The third blank C-3 is connected to the first blank C-1 in a like manner, that is to say that the tab 34 on the blank C-3 is interlocked with the slit 30 of the blank C-1. This creates a somewhat circular arrangement of the blanks C-1, C-2 and C-3, but even so, the tab 34 of the third blank C-3 remains detached from the slit 30 of the second blank C-2. The elastic band B is looped several times between the detached ends of the blanks C-2 and C-3, where it passes through the closely spaced holes 44 and 45 in each. Another elastic band B extends between the holes 46 in the blank C-1, the center of the three blanks C-1, C-2, C-3.

The shade F fits over the user's head, resting on it along the panels 22 of the three interlocked blanks C-1, C-2, C-3, for the elastic band B which is looped several times between the blanks C-2 and C-3 urges all three abutment panels 22 against the user's head, with the panel 22 of the blank C-1 being against the forehead and the panels 22 of the blanks C-2 and C-3 being against the sides of the head. In other words, the elastic band B renders the sun shade F adjustable so that it can fit heads of varying size. The main panels 20 of the three blanks C-1, C-2 and C-3 project obliquely outwardly beyond the forehead, sides, and back of the user's head, each being stabilized by its lip 24 which turns upwardly or at least outwardly along its outer score line 18. In other words, each lip 24, when turned back toward its respective main panel 20 so as to be disposed at an angle with respect to the panel 20, prevents the panel 20 from assuming an excessive angle along its other score line 16 and thereby turning too far downwardly. The other elastic band B, that is the one that attaches to the panel C-1, extends around the back of the user's head or under the user's chin and holds the sun shade F on the user's head.

Finally, the blank C may be used as a fan for moving air in front of the user's face on still days.

The panel 20 for the blank C is quite large and visible irrespective of whether the blank C is used as the sun visor A, the megaphone D, the hat E or the sunshade F, and as such provides an excellent location for displaying advertising messages or other information.

Figure 11:
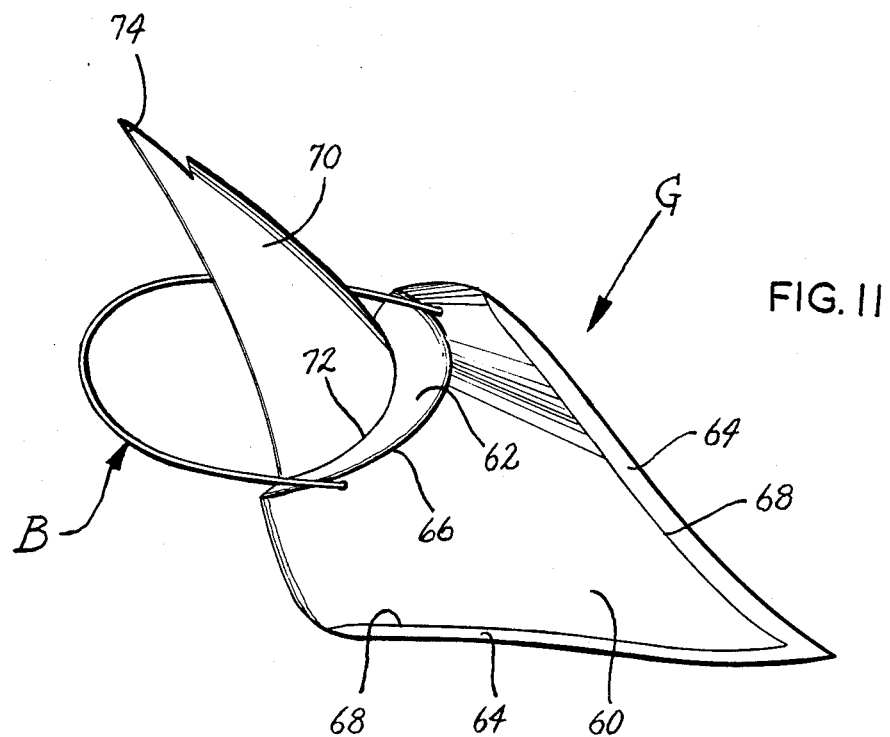
FIG. 11 is a perspective view of a modified sun visor.

The invention, while being a visor, need not have that traditional appearance of a visor. Indeed, it may take on less orthodox shapes, perhaps the shape of an animal that may be the mascot of a sports team or university. For example, a modified visor G (FIG. 11) resembles the head of a bird, such as a cardinal, but like the visor A, it has a main panel 60, an abutment panel 62 at one end of the main panel 60 and a lip 64 at the other end of the main panel 60. The abutment panel 62 turns downwardly from the main panel 60 along a rear score line 66 and follows the contour of the user's forehead along which it is located when the visor G is in use. The lip 64 turns upwardly from the opposite or forward end of the main panel along a score line 68, and as such maintains the main panel in an outwardly directed orientation with respect to the abutment panel 62 and the user's forehead. Otherwise the main panel 60 would drop downwardly in front of the user's face to obscure his vision.

While the score line 66 resembles a simple arc—and well it should for it is along the user's forehead—the other score line 68 has two segments which converge forwardly, and this imparts a V-shaped configuration to the main panel 60. Indeed, the main panel 60 resembles the head of a bird with the region of convergence for the segments of the score line 68 being the beak. The greater surface area created in the main panel 60 by reason of the V-shaped configuration may be marked to resemble the eyes, beak and other features of a bird, or it may bear advertising messages, or both.

In addition to the two panels 60 and 62 and the lip 64 the visor G has a decorative panel 70 which is connected to the abutment panel 62 along a score line 72 where it turns upwardly along the abutment panel 60 and projects above it, terminating at a peak 74. The decorative panel 70 thus resembles the head feathers of a bird. Actually when the visor G is in use, the decorative panel 70 is against the user's forehead, whereas the abutment panel is for the most part interposed between the decorative panel 70 and the main panel 60.

The visor G is held against the user's forehead by an elastic band B which attaches to the main panel 60 inwardly from its edge and extends around the user's head.

This invention is intended to cover all changes and modifications of the example of the invention herein chosen for purposes of the disclosure which do not constitute departures from the spirit and scope of the invention.

What is claimed is:

1. A sun visor formed from a flexible sheet-like material, said visor comprising: a main panel having an arcuate inner margin located along a score line in the sheet-like material and an arcuate outer margin located along another score line in the sheet-like material, the main panel being bowed with the convex surface so formed being presented outwardly; an abutment panel connected to the main panel along the arcuate inner margin and turned abruptly downwardly with respect to the main panel at the score line that forms the inner margin so that an acute angle exists between the abutment panel and the main panel, the abutment panel being bowed to generally conform to a user's forehead and being about as long as the user's forehead is wide; and a lip connected to the main panel along the arcuate outer panel and turned upwardly with respect to the main panel at the score line that forms the outer margin such that a distinct obtuse angle exists between the lip and the main panel, the upwardly turned lip serving to stiffen the bowed main panel when the abutment panel is against a user's forehead so as to prevent the main panel from folding against the abutment panel and blocking the user's vision.

2. A visor according to claim 1 wherein the lip is continuous along the outer arcuate margin of the main panel.

3. A visor according to claim 2 wherein the lip extends substantially from one side of the main panel to the other side.

4. A visor according to claim 1 wherein the abutment panel is bowed toward the lip and extends substantially the full length of the arcuate inner margin.

5. A visor according to claim 1 wherein the abutment panel has one margin along the inner margin of the main panel and another free margin which is arcuate and spaced from the inner margin of the panel, the abutment panel extending from substantially one end of the inner margin for the panel to substantially the other end and being continuous intermediate its ends.

6. A visor according to claim 5 wherein the abutment panel has rounded corners at the end of its arcuate free margin.

7. A visor according to claim 1 and further comprising means for holding the ends of the main panel together.

8. A visor according to claim 1 wherein the abutment panel has a lower margin and further comprising a decorative panel attached to the abutment panel along the lower margin thereof and projecting upwardly beyond the main panel.

9. A blank suitable for conversion into a sun visor, said blank being formed from a thin sheet of flexible material and having arcuate inner and outer margins which are generally parallel and side margins which diverge from the inner margin to the outer margin, the blank also having inner and outer score lines which generally follow the contour of the inner and outer margins and extend from one side margin to the other so as to divide the blank into a main panel located between the two score lines, an abutment panel located between the inner score line and the arcuate inner margin and being long enough to extend generally across a user's forehead, but not substantially beyond the forehead, and a lip located between the outer score line and the arcuate outer margin, whereby the abutment panel may be folded downwardly with respect to the main panel along the inner score line and the lip may be folded upwardly with respect to the main panel along the outer score line to convert the blank into a sun visor, the abutment panel and lip being substantially narrower than the main panel.

10. The blank according to claim 9 wherein the inner score line extends from one side margin to the other side margin.

11. The blank according to claim 10 wherein the side margins are straight.

12. The blank according to claim 9 wherein the arcuate inner and outer margins merge into the side margins at rounded corners; wherein the inner score line extends from one side margin to the other beyond those rounded corners that are at the ends of the arcuate inner margin; and wherein the outer score line extends from the rounded corner at one end of the arcuate outer margin to the rounded corner at other end of that margin.

13. The blank according to claim 12 wherein the tab is configured to interlock with the portion of the main panel in which the slit is located.

14. A megaphone or hat comprising the blank of claim 13 deformed into a conical configuration with the tab along one side margin received in the slit along the other side margin, whereby the tab may serve as a handle for the megaphone.

15. A sun shade comprising at least two of the sun visors of claim 1 with the tab of the one sun visor being inserted into and interlocked with the slit of the other sun visor.

16. A sun visor formed from a flexible sheet-like material, said visor comprising: a main panel having an arcuate inner margin and an arcuate outer margin which extends between ends of the panel, the main panel being bowed with the convex surface so formed being presented outwardly, the main panel at one of its ends being provided with a tab and at the other of its ends with a slit, the tab being configured to fit into and interlock with the slit; an abutment panel connected to the main panel along the arcuate inner margin and turned downwardly with respect to the main panel; and a lip connected to the main panel along the arcuate outer margin and turned upwardly with respect to the main panel.

17. A sun visor formed from a flexible sheet-like material, said visor comprising: a main panel having an arcuate inner margin and an arcuate outer margin and being bowed with the convex surface so formed being presented outwardly; an abutment panel connected to the main panel along the arcuate inner margin and turned downwardly with respect to the main panel, the abutment panel having a lower edge; a lip connected to the main panel along the arcuate outer margin and turned upwardly with respect to the main panel; and attaching means for holding the visor on a user's head with the abutment panel against the user's forehead and the lower edge away from the forehead for comfort, the attaching means including an elastic band which is connected to the main panel near the arcuate inner margin thereof but inwardly from the ends of main panel and which extends around the back of the user's head.

18. A blank suitable for conversion into a sun visor, said blank being formed from a thin sheet of flexible material and having arcuate inner and outer margins which are generally parallel, and side margins which diverge from the inner margin to the outer margin, the blank also having inner and outer score lines which generally follow the contour of the inner and outer margins and divide the blank into a main panel located between the two score lines, an abutment panel located between the inner score line and the arcuate inner margin and a lip located between the outer score line and the arcuate outer margin, whereby the abutment panel may be folded downwardly with respect to the main panel along the inner score line and the lip may be folded upwardly with respect to the main panel along the outer score line to convert the blank into a sun visor, the main panel near one of the side margins having a slit in the configuration of a tab which projects generally toward the side margin along which it is located, the main panel near its other side margin having another slit which is generally parallel to that margin and is long enough to receive the tab.

19. The combination comprising: a blank suitable for conversion into a sun visor, said blank being formed from a thin sheet of flexible material and having arcuate inner and outer margins which are generally parallel and side margins which diverge from the inner margin to the outer margin, the blank also having inner and outer score lines which generally follow the contour of the inner and outer margins and divide the blank into a main panel located between the two score lines, an abutment panel located between the inner score line and the arcuate inner margin and a lip located between the outer score line and the arcuate outer margin, whereby the abutment panel may be folded downwardly with respect to the main panel along the inner score line and the lip may be folded upwardly with respect to the main panel along the outer score line to convert the blank into a sun visor; and a band attached to the main panel of the blank near the arcuate inner score line.

20. A sun shade comprising at least two sun visors attached end-to-end, each sun visor being formed from a flexible sheet-like material and comprising: a main panel having an arcuate inner margin and an arcuate outer margin and being bowed with the convex surface so formed being presented outwardly; an abutment panel connected to the main panel along the arcuate inner margin and turned downwardly with respect to the main panel; a lip connected to the main panel along the arcuate outer margin and turned upwardly with respect to the main panel; and holding means for holding the sides of the main panel together or for holding the side of the main panel for one together or for holding the side of the main panel for one visor to the end if the main panel of another visor; the two sun visors being attached end-to-end at their respective holding means.

21. The combination including: a sun visor formed from a flexible sheet-like material, said visor comprising: a main panel having an arcuate inner margin located along a score line in the sheet-like material and an arcuate outer margin located along another score line in the sheet-like material, the main panel being bowed with the convex surface so formed being presented outwardly, an abutment panel connected to the main panel along the arcuate inner margin and turned abruptly downwardly with respect to the main panel at the score line that forms the inner margin, and a lip connected to the main panel along the arcuate outer margin and turned upwardly with respect to the main panel at the score line that forms the outer margin such that a distinct angle appears in the sheet material at the score line for the outer margin; and further including a band attached to the main panel at two spaced apart locations along the inner margin of the main panel, the band being of a size suitable for passing around the back of a user's head so as to hold the visor generally above the user's eyes with its abutment panel against the user's forehead.

22. The combination according to claim 21 wherein the band is elastic.

23. The combination according to claim 22 wherein the locations at which the band is attached to the main panel are spaced substantially inwardly from the sides of the main panel.

* * * * *

UNITED STATES PATENT AND TRADEMARK OFFICE
CERTIFICATE OF CORRECTION

PATENT NO. : 4,850,054
DATED : July 25, 1989
INVENTOR(S) : Kim C. Sutton

It is certified that error appears in the above-identified patent and that said Letters Patent is hereby corrected as shown below:

Column 3, line 37, "4B" should be "48".

Column 4, line 40, "pane 22" should be "panel 22".

Column 5, line 13, "line 1B" should be "line 18".

Column 9, lines 25 & 26, delete "together or for holding the side of the main panel for one". That part has been duplicated.

Signed and Sealed this

Eighth Day of May, 1990

*Attest:*

HARRY F. MANBECK, JR.

*Attesting Officer*  *Commissioner of Patents and Trademarks*